United States Patent
Liu et al.

(10) Patent No.: US 9,260,668 B2
(45) Date of Patent: Feb. 16, 2016

(54) METHOD FOR REVAMPING AN HF OR SULPHURIC ACID ALKYLATION UNIT AND METHOD FOR THE PRODUCTION OF ALKYLATE

(75) Inventors: Zhichang Liu, Changping Beijing (CN); Chunming Xu, Changping Beijing (CN); Rui Zhang, Changping Beijing (CN); Xianghai Meng, Changping Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 133 days.

(21) Appl. No.: 13/388,499

(22) PCT Filed: Jul. 9, 2010

(86) PCT No.: PCT/EP2010/059915
§ 371 (c)(1),
(2), (4) Date: Mar. 13, 2012

(87) PCT Pub. No.: WO2011/006848
PCT Pub. Date: Jan. 20, 2011

(65) Prior Publication Data
US 2012/0172646 A1    Jul. 5, 2012

(51) Int. Cl.
*C07C 2/74* (2006.01)
*C10G 29/20* (2006.01)
*C07C 2/60* (2006.01)

(52) U.S. Cl.
CPC ............. *C10G 29/205* (2013.01); *C07C 2/60* (2013.01); *C07C 2527/053* (2013.01);
(Continued)

(58) Field of Classification Search
USPC ............ 502/35, 27, 32, 20, 22, 150; 585/709, 585/710, 721, 722, 457, 719, 723, 730, 585/731; 422/620, 622, 619
See application file for complete search history.

(56) References Cited

U.S. PATENT DOCUMENTS 7,256,152 B2 *   8/2007   Olivier-Bourbigou et al. .............................. 502/150
7,285,698 B2    10/2007   Liu et al. ....................... 585/721
(Continued)

FOREIGN PATENT DOCUMENTS

CN          1432627        7/2003
CN        101244972        8/2008
(Continued)

OTHER PUBLICATIONS

Liu, Z. et al.; "Ionic Liquid Alkylation Process Produces High-Quality Gasoline"; Oil and Gas Journal, vol. 104, Issue 40; pp. 52-55; Oct. 23, 2006.
(Continued)

*Primary Examiner* — In Suk Bullock
*Assistant Examiner* — Philip Louie

(57) ABSTRACT

The present invention provides a method for revamping an HF or sulphuric acid alkylation unit to an ionic liquid alkylation unit, wherein the HF or sulphuric acid alkylation unit comprise at least: —a reactor unit for contacting catalyst and hydrocarbon reactants; —a separator unit for separating a reactor effluent into a catalyst phase and an alkylate-comprising hydrocarbon phase; —a fractionator unit for fractionating the alkylate-comprising hydrocarbon phase into at least one stream comprising alkylate; —a catalyst phase recycle means to recycle at least part of the catalyst phase from the separator unit to the reactor unit; which method includes: —adapting the catalyst phase recycle means by providing a means for acid injection and/or a means for halohydrocarbon injection into the catalyst recycle means. The invention further provides a method for the production of alkylate.

17 Claims, 1 Drawing Sheet

Figure 1:
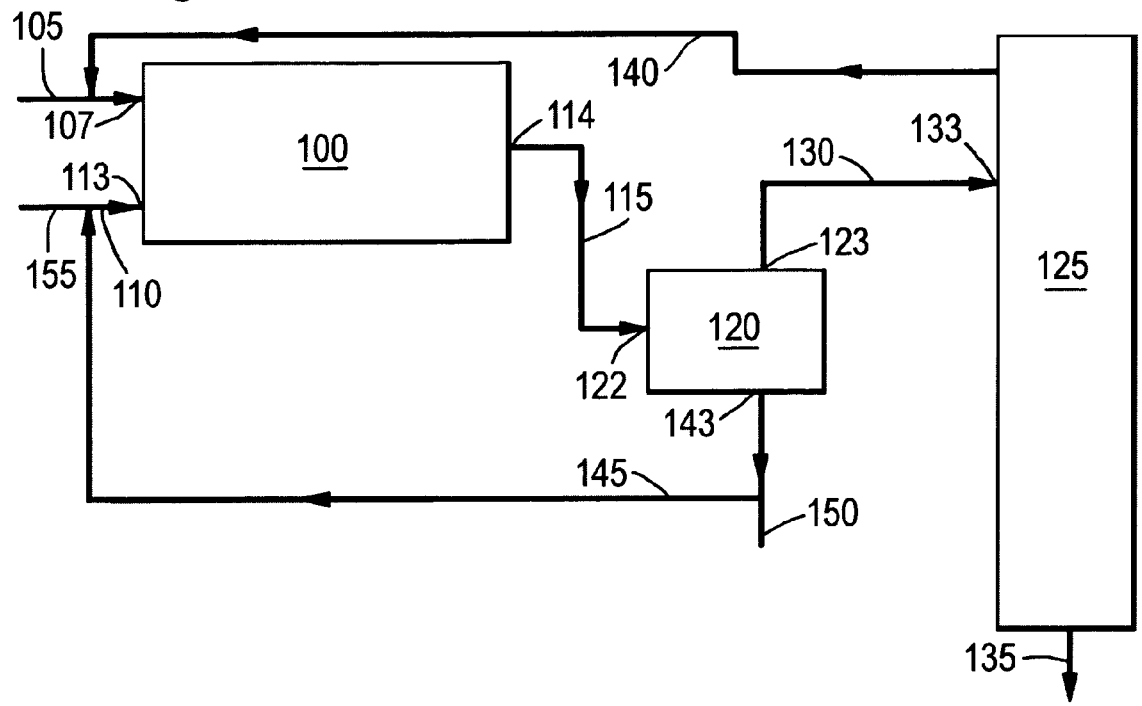

(52) U.S. Cl.
CPC ...... *C07C 2527/055* (2013.01); *C07C 2527/06* (2013.01); *C07C 2527/122* (2013.01); *C07C 2527/128* (2013.01); *C07C 2527/135* (2013.01); *C07C 2527/138* (2013.01); *C07C 2527/25* (2013.01); *C07C 2531/02* (2013.01); *C10G 2300/1081* (2013.01); *C10G 2300/1092* (2013.01); *C10G 2300/70* (2013.01); *Y10T 29/49716* (2015.01)

(56) References Cited

U.S. PATENT DOCUMENTS

| | | | |
|---|---|---|---|
| 7,432,409 | B2 | 10/2008 | Elomari et al. |
| 2005/0119423 | A1 | 6/2005 | Bergman et al. |
| 2006/0135839 | A1 | 6/2006 | Elomari et al. |
| 2007/0142213 | A1* | 6/2007 | Elomari et al. ............ 502/53 |
| 2007/0142216 | A1* | 6/2007 | Harris et al. ............... 502/53 |
| 2007/0225538 | A1* | 9/2007 | Elomari ..................... 585/727 |
| 2008/0146858 | A1 | 6/2008 | Elomari et al. |

FOREIGN PATENT DOCUMENTS

| | | |
|---|---|---|
| GB | 0647155 | 4/1995 |
| WO | WO 2004018086 A1 * | 3/2004 |

OTHER PUBLICATIONS

Liu, Y et al.; "Alkylation of Isohutene with 2-butene Using Composite Ionic Liquid Catalysts"; Applied Catalysis A: General, Elsevier Science, vol. 346, No. 1-2; pp. 189-193; Aug. 31, 2008.

Kumar P, et al.; "Production of Alkylated Gasoline Using Ionic Liquids and Immobilized Ionic Liquids"; Applied Catalysis A: General, Elsevier Science; vol. 304, pp. 131-141; May 10, 2006.

Huang, C.P. et al; "Effects of Additives on the Properties of Chloroaluminate Ionic Liquids Catalyst for Alkylation of Isobutane and Butene"; Applied Catalysis A: General, Elsevier Science; vol. 277, No. 1-2; pp. 41-43; Dec. 8 ,2004.

\* cited by examiner

METHOD FOR REVAMPING AN HF OR SULPHURIC ACID ALKYLATION UNIT AND METHOD FOR THE PRODUCTION OF ALKYLATE

PRIORITY CLAIM

The present application claims priority from PCT/EP2010/059915, filed 9 Jul. 2010, which claims priority from Chinese application 200910089442.7, filed 17 Jul. 2009 and PCT/CN2009/000885 filed 6 Aug. 2009.

The present invention provides a method for revamping an HF or sulphuric acid alkylation unit and a method for the production of alkylate.

There is an increasing demand for alkylate fuel blending feedstock. As a fuel-bending component alkylate combines a low vapour pressure, no olefin or aromatic content with high-octane properties.

Almost all alkylate is produced by reacting isobutane with butene in the presence of a suitable acidic catalyst. The most used catalysts are HF (hydrofluoric acid) and sulphuric acid. Although well established, these processes suffer numerous disadvantages. In case of HF, stringent health and safety measures must be applied requiring significant investments. In case of sulphuric acid, the large consumption of catalyst and the need to provide utilities for refrigeration are unfavourable from an economic standpoint.

Recently, the alkylation of isoparaffins with olefins using an ionic liquid catalyst has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor unit and the alkylate is formed by contacting the reactants with a composite ionic liquid under alkylation conditions. The reactor effluent is separated into a hydrocarbon phase and an ionic liquid phase. The ionic liquid phase is recycled to the reactor unit while the hydrocarbon phase is treated to retrieve the alkylate.

Current alkylation units have been specifically designed for either HF or sulphuric acid (also referred to as SA) catalyst and are not optimally suited for use of a different catalyst such as an ionic liquid (also referred to as IL) catalyst. In for instance Liu et al. (Z. Liu, R. Zhang, C. Xu, R. Xia, Ionic liquid alkylation process produces high-quality gasoline, Oil and Gas Journal, vol 104, Issue 40, 2006) it is mentioned that it is possible to retrofit a sulphuric acid alkylation unit for use of an IL catalyst. In Liu et al., it is proposed to add a surge tank for IL recycle and to modify the settler internals to enhance separation of the IL. However, it was found by Liu that the performance of the retrofitted alkylation unit was less than optimal.

Therefore, there is a need in the art for an improved method for revamping HF or SA alkylation unit to an IL alkylation unit.

It has now been found that the less than optimal results reported by Liu et al, are at least in part caused by the different deactivation/reactivation behaviour of the IL catalyst.

Therefore, the present invention provides a method for revamping an HF or sulphuric acid alkylation unit to an ionic liquid alkylation unit, wherein the HF or sulphuric acid alkylation unit comprise at least:

a reactor unit for contacting catalyst and hydrocarbon reactants;

a separator unit for separating a reactor effluent into a catalyst phase and an alkylate-comprising hydrocarbon phase;

a fractionator unit for fractionating the alkylate-comprising hydrocarbon phase into at least one stream comprising alkylate;

a catalyst phase recycle means to recycle at least part of the catalyst phase from the separator unit to the reactor unit; which method includes:

adapting the catalyst phase recycle means by providing a means for acid injection and/or a means for halohydrocarbon injection into the catalyst recycle means.

In a second aspect the invention provides a method for the production of alkylate comprising:

a) in an alkylation process for producing an alkylate from a feed mixture comprising isobutene and olefin in the presence of an ionic liquid catalyst and under alkylation conditions, separating off all or a portion of the ionic liquid catalyst from the process for producing an alkylate;

b) injecting a hydrohalide or halohydrocarbon into the separated portion of the acidic ionic liquid; and c) re-introducing the acidic ionic liquid, into which the hydrohalide or halohydrocarbon has been introduced, into the process for producing an alkylate of step (a).

In the first aspect the present invention relates to a method for revamping an HF or SA alkylation unit to an IL alkylation unit. Reference herein to revamping is to modifying or adapting an existing unit or process line-up designed for operating a specific process, such that it is suitable for operating another process. The obtained IL alkylation unit may used operate the method according to the second aspect of the invention to produce alkylate in an alkylation process by reacting an isoparaffin with an olefin in the presence of an IL catalyst under alkylation conditions. Typical IL alkylation conditions (or process conditions) are known in the art, whereby it will be appreciated that actual operational process conditions are among others dependent of the exact composition of the reactants and catalyst.

In the alkylation process, the temperature in the reactor unit is preferably in the range of from −20 to 100° C., more preferably in the range of from 0 to 50° C., however the temperature must be high enough to ensure that the ionic liquid is in its liquid form.

To suppress vapour formation in the reactor, the alkylation process is performed under pressure, preferably the pressure in the reactor is in the range of from 0.1 to 1.6 MPa.

The alkylation process may be a semi-continuous or continuous process. Typically, the isoparaffin is isobutane or isopentane and the olefin is an olefin comprising in the range of from 2 to 8 carbon atoms, more preferably of from 3 to 6 carbon atoms, even more preferably 4 or 5 carbon atoms, the latter two are further also referred to a C4 alkene and C5 alkene. Examples of suitable olefins include, propene, 1-butene, 2-butene, isobutene, 1-pentene, 2-pentene, 2-methyl-1-butene, 3-methyl-1-butene, 2-methyl-2-butene or a mixture thereof.

In an IL alkylation process, fresh isoparaffins and olefins are supplied to the process in a molar ratio, which is preferably 1 or higher, and typically in the range of from 1:1 to 40:1, more preferably 1:1 to 20:1. In the case of continuous reaction, the excess isoparaffin can be recycled to the reactor unit by recycling one or more isoparaffin-comprising streams.

Reference herein below to downstream is to the direction of the fluid flow path from the reactor unit to the fractionator unit. Reference herein upstream is to the opposite direction, i.e. from the fractionator unit to the reactor unit.

Existing HF and SA alkylation units comprise at least a reactor unit for contacting the reactants with the catalyst. The reactor unit preferably comprises at least one reactant inlet and at least one reactor effluent outlet. Preferably, the reactor unit also comprises at least one catalyst inlet. A typical reactor unit provided in sulphuric alkylation unit is a so-called Stratco contactor. In e.g. a Stratco contactor, the hydrocarbon reactants are introduced into an U-shaped reactor fluid flow path together with the catalyst. For HF alkylation typical reactors include e.g. Stratco contactors, gravity circulation reactors and emulsion reactors.

Generally, cooling tubes are provided in the reactor fluid flow path to remove the heat generated by the exothermic alkylation reaction. Alternatively, cooling is applied to the acid recycle stream. The effluent of the reactor unit is a mixture of catalyst and a hydrocarbon phase, the latter comprising an alkylate and unreacted reactants, predominantly isoparaffin.

The effluent of the reactor unit is normally provided to a separator unit to separate the reactor effluent into a catalyst phase and an alkylate-comprising hydrocarbon phase. Preferably, the separator unit comprises at least one inlet, typically for the reactor effluent or a stream generated there from, and at least one catalyst phase outlet and at least one alkylate-comprising hydrocarbon phase outlet.

The separator unit serves to separate the effluent of the reactor unit into an alkylate-comprising hydrocarbon phase and a catalyst phase. Preferably, the separator unit used in the HF and SA alkylation units to be revamped is a settler unit. Due to the low affinity of the HF and SA catalyst for hydrocarbons, the two phases separate readily under the influence of gravity. Reference herein to a settler unit is to any separator unit that separates two liquid phases under the influence of gravity. Actually, HF, SA and IL catalysts all have a density, which is higher than that of the hydrocarbon phase, therefore the reactor effluent is typically separated in the settler in an upper hydrocarbon phase and a lower catalyst phase.

In case of SA alkylation, catalyst phase recycle means are provided to recycle SA catalyst from the settler unit to the reactor unit. Typically, to maintain catalyst activity, part of the SA catalyst is removed from the process as spent catalyst and fresh SA catalyst is added to keep catalyst levels and activity intact.

In case of HF alkylation, the HF catalyst is regenerated and recycled to the process for reuse. For this reason, an HF alkylation unit comprises catalyst phase recycle means to recycle the HF catalyst, combined a separate regeneration.

In both SA and HF alkylation, the alkylate-comprising hydrocarbon phase, which was obtained in the settler is, at least in part, provided to a fractionator unit to obtain the alkylate. The fractionator unit preferably comprises at least one alkylate-comprising hydrocarbon phase inlet. The fractionator unit, typically, comprises one or more distillation sub-units, including for instance a main fractionator (also referred to in the art as iso-stripper), an acid stripper and/or a depropaniser.

Following the fractionation, the obtained alkylate may be used to prepare avgas or as a blending component for gasoline. The hydrocarbon phase may also comprise significant amounts of unreacted isoparaffin. Preferably, such isoparaffin is at least partly recycled back to the reactor unit, via a provided means for recycling isoparaffin from the fractionator unit to the reactor. Other hydrocarbon streams may also be obtained by fractionation of the hydrocarbon phase, such a n-paraffin-comprising stream.

In existing HF or SA alkylation units means are provided to allow the reactants and catalyst to enter the reactor and to provide the reactor effluent to the separator unit and subsequently the alkylate-comprising hydrocarbon phase to the fractionator unit. It is not necessary to pass the reactor effluent directly from the reactor unit to the separator unit. The reactor effluent may undergo intermediate treatment such as cooling or heating in a heat exchanger. The same applies for the the alkylate-comprising hydrocarbon phase being provided to to the fractionator unit. Typically, a fluid flow path for the reactants, products and catalyst is created by providing means to introduce reactants and catalyst to the reactor unit. In addition, means are provided to provide reactor effluent from the reactor effluent outlet of the reactor unit to the reactor effluent inlet of a separator unit located downstream from the reactor unit in the fluid flow path. Also, means are provided to provide an alkylate-comprising hydrocarbon phase from the alkylate-comprising hydrocarbon phase outlet of the separator unit to the alkylate-comprising hydrocarbon phase inlet of a fractionator unit located downstream from the separator unit in the fluid flow path and catalyst phase recycle means are provided to recycle catalyst from the settler unit to the reactor unit.

Ionic liquids are known in the art for their ability to catalyse alkylation reactions. The catalyst used in the present invention is a composite ionic liquid comprising cations derived from a hydrohalide of an alkyl-containing amine, imidazolium or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium ($NEt_3H^+$) and methyl-diethyl-ammonium cations ($MeNEt_2H^+$) or

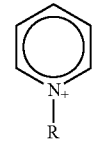

The anions of the composite ionic liquid are preferably aluminium based Lewis acids, in particular aluminium halides, preferably aluminium (III) chloride or aluminium (III) bromide. Due the high acidity of the aluminium chloride and aluminium bromide Lewis acids it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples or suitable metals include copper, iron, zinc, nickel, cobalt, molybdenum, titanium, silver, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285, 698. Particularly preferred catalysts are acidic ionic liquid catalysts comprising a coordinate anion derived from aluminium(III) chloride and copper(II) chloride or aluminium(III) chloride and copper(I) chloride.

In the method according to the first aspect of the present invention a means to rejuvenate the ionic liquid catalyst are provided. In the method according to the second aspect of the present invention the IL catalyst is rejuvenated while operating an alkylation process.

In case of SA alkylation, the spent SA catalyst is discarded or regenerated off-site. Therefore, a conventional SA alkylation unit will not comprise any catalyst regeneration unit. In HF alkylation, the catalyst is recycled and regenerated. However, HF regeneration takes place by removal of water and acid soluble oils (ASO) from the HF. Such regeneration treatment is not sufficient to regenerate an IL catalyst. In the catalysis of the alkylation reaction using ionic liquids, Lewis and Brönsted acids both play a part, the Lewis acidity of the ionic liquid mainly determining the selectivity of the product obtained, whilst the Brönsted acidity of the ionic liquid is the determining factor as to whether or not carbocations can be generated. It has been observed that, during the alkylation process relying on ionic liquids as catalysts, the alkylate products generally contain between 0.001-1 wt % of halides, in particular alkylhalides. This is an indication that as the reaction progresses, the Brönsted acid within the ionic liquid is gradually lost and as a result the IL catalyst loses activity. Therefore, the present invention involves the rejuvenation (or regeneration) of the Brönsted acid acidity of the ionic liquid. In order to restore at least part of the IL catalyst activity, i.e. its Brönsted acid acidity, it is preferred to introduce a suitable acid to the, at least partly, deactivated catalyst. Preferably, such acid is a hydrogen halide (also referred to as halo acid), more preferably hydrochloric acid (also referred to as hydrogen chloride or HCl) or hydrobromic acid (also referred to as hydrogen bromide or HBr). For instance, the catalyst may be contacted with hydrogen chloride to rejuvenate the catalyst. This can be done by introducing hydrogen chloride or another suitable acid into the reactor unit or into at least part of the reactor effluent, which comprises at least part of the acidic ionic liquid catalyst. Preferably, hydrogen chloride or another suitable acid is contacted with at least part of the reactor effluent, which comprises at least part of the acidic ionic liquid catalyst. More preferably, the hydrogen chloride or another suitable acid is contacted with the IL catalyst after separation from the hydrocarbons in the settler unit.

In the method according to the first aspect of the present invention a catalyst phase recycle means for providing HF or SA catalyst from the separator unit to the reactor unit is adapted, by additionally providing a means for acid injection into the catalyst phase recycle means, i.e. between the separator unit and the reactor unit. Suitable means for acid injection comprise gas and liquid injectors or gas bubblers, preferably combined with a suitable storage vessel for the acid. For instance, in case of a hydrogen chloride injection, the means for injecting an acid may comprise a gas injector or bubbler fluidly connected to a vessel for storing gaseous hydrogen chloride. Suitably circulation means comprising a venturi absorber may be provided to circulate at least part of the catalyst phase recycle and mix it with the gas cap using the venturi absorber. Preferably means are provided to further mix the acid with the IL.

The hydrogen chloride reacts with the acidic ionic liquid catalyst. Hydrogen chloride is added until no hydrogen chloride is consumed any longer, i.e. until saturation. Hydrogen chloride consumption can be followed by measuring the pressure decrease. Preferably, the addition of hydrogen chloride is done in regular steps, while measuring the pressure in between each addition step. By adding the hydrogen chloride in small steps the creation of an undesired hydrogen chloride gas cap upon saturation is reduced. To follow the hydrogen chloride pressure it is preferred that a means for measuring the pressure is provided in the catalyst recycle or the reactor unit.

Although some gaseous hydrogen chloride in the reactor unit may be tolerated, it is undesired to accumulate unreacted gaseous hydrogen chloride in the reaction system as a result of over-saturation of the acidic ionic liquid with hydrogen chloride. Residual gaseous hydrogen chloride may be purged from the reaction system by providing for instance a means for flushing with an inert gas such as nitrogen. However, this would require additional means for providing nitrogen gas and subsequent storage and treatment of hydrogen chloride-contaminated nitrogen gas. In addition, part of the hydrogen chloride is provided for rejuvenation is lost. Preferably, such hydrogen chloride accumulation is reduced by mixing additional spent acidic ionic liquid catalyst, e.g. in the form of a spent catalyst-comprising stream, into the rejuvenated and recycled acidic ionic liquid catalyst phase effluent, i.e. the recycled catalyst phase comprising added hydrogen chloride. Reference herein to spent acidic ionic liquid catalyst is to an acidic ionic liquid catalyst, which has been used as a catalyst in a chemical reaction and has not yet been rejuvenated with hydrogen chloride. By allowing the spent acidic ionic liquid to react with the gaseous hydrogen chloride present due to initial over-saturation, at least part of the remaining hydrogen chloride may be consumed. The spent ionic liquid catalyst may be introduced from an external source, however, preferably means are provided in the catalyst phase recycle means allow part of the ionic liquid catalyst to bypass the rejuvenation and subsequently mix the rejuvenated and bypassed streams, preferably in between 1 to 99% of the IL is subjected to the acid injection rejuvenation, more preferably 1 to 50%.

Alternatively, the IL catalyst can be rejuvenated or regenerated by injecting a halohydrocarbon into the IL in the catalyst recycle means. Preferably, the halohydrocarbon contains 4 to 8 carbon atoms. Preferably the halide and the carbon connecting to the halide in the halohydrocarbon is a secondary carbon atom or tertiary carbon atom. Suitable halohydrocarbons include chloroalkanes or bromoalkanes containing 4 carbon atoms. Preferably, the halohydrocarbons are halogenated alkanes that satisfy the above requirements, especially preferred halogenated alkanes have between 4 to 8 carbon atoms, such as 2-chloro (bromo)-2-methyl-propane, 2-chloro (bromo)-2-methyl-hexane, 2-bromobutane and 2-chlorobutane. The halohydrocarbon injection can replace the acid injection or may be done in conjunction with the acid injection. The halohydrocarbon injection may be done using a separate suitable means for halohydrocarbon injection or may be effected using the same means as used for injecting an acid.

The features and measures described herein above for the acid injection for rejuvenating the catalyst also apply mutatis mutandis for the halohydrocarbon injection.

In order to add sufficient acid or halohydrocarbon to the IL, it is preferred that the means for acid injection and/or the means for halohydrocarbon injection are suitable to inject acid in a quantity of between 0.01-1 wt % of the alkylate yield, i.e. the actual quantity of alkylate produced, more preferably between 0.05-0.5 wt %, based on the halide mass, and/or halohydrocarbon in a quantity of between 0.01-1 wt % of the alkylate yield, i.e. the actual quantity of alkylate produced, more preferably between 0.05-0.5 wt %, based on the halide mass. Reference herein to the alkylate is to the hydrocarbon product that is left after the alkylation process and after any excess C4 alkane has been recovered. When an insufficient quantity of hydrohalide or halohydrocarbon is used it is not possible to maintain catalytic activity. However, when an excessive quantity of acid or halohydrocarbon is used, this affects the selectivity of the alkylate product.

In the second aspect of the invention, a method is provided, wherein in an alkylation process using an IL catalyst, part or all of the IL catalyst is treated to rejuvenate the IL catalyst. The method according to the second aspect of the invention may be operated in any suitable alkylation unit. Preferably, this is a revamped SA or HF alkylation unit according to the first aspect of the invention, however it may also be another alkylation unit equipped with suitable means for separating off part of the IL catalyst and injecting an acid or halohydrocarbon into the separated IL catalyst.

All features and measures described herein above with respect to the first aspect of the invention relating to the reactants, products, alkylation condition and any other features and measures relating to the operation of an alkylation process apply mutatis mutandis to the method according to the second method according to the invention.

In the method according to the second aspect of the invention, an alkylation process is operated using an IL catalyst. During the operation of the alkylation process, all or, preferably, a portion of the IL catalyst is separated off from the alkylation process. Subsequently, a hydrohalide or halohydrocarbon is injected into the separated portion of the IL to rejuvenate (or regenerate) the IL catalyst by restoring part of its Brönstad acid acidity. Preferably, the IL and hydrohalide or halohydrocarbon are mixed following the injection.

Following the acid or halohydrocarbon injection the IL, into which the acid or halohydrocarbon has been introduced, is re-introduced into the process for producing an alkylate of step (a).

Preferably, a quantity is injected of between 0.01-1 wt % of the alkylate yield, i.e. the actual quantity of alkylate produced, more preferably between 0.05-0.5 wt %, based on the halide mass, and/or halohydrocarbon in a quantity of between 0.01-1 wt % of the alkylate yield, i.e. the actual quantity of alkylate produced, more preferably between 0.05-0.5 wt %, based on the halide mass. Reference herein to the alkylate is to the hydrocarbon product that is left after the alkylation process and after any excess C4 alkane has been recovered. When an insufficient quantity of hydrohalide or halohydrocarbon is used it is not possible to maintain catalytic activity. However, when an excessive quantity of acid or halohydrocarbon is used, this affects the selectivity of the alkylate product.

Preferably, the source of cations within the IL is a hydrohalide amine containing alkyls, halogenated imidazole or halogenated pyridine, the source of the anions being one or more metallic compounds.

Preferably, the anions within the aforementioned acidic ionic liquid come from two or more metallic compounds, where at least one of these metallic compounds is either aluminium chloride or aluminium bromide, the other metallic compounds being halides, sulphates or nitrates of copper, iron, zinc, nickel, titanium or silver.

Preferably, a hydrohalide is injected, more preferably hydrogen chloride or hydrogen bromide.

Equally preferable, a halohydrocarbon is injected, more preferably a chloroalkane or a bromoalkane containing at least 4 carbon atoms.

Optionally, both a hydrohalide and a halohydrocarbon are injected, separately or as a mixture.

Preferably, the halohydrocarbon contains 4 to 8 carbon atoms and a halide and the carbon connecting to the halide in the halohydrocarbon is a secondary carbon atom or tertiary carbon atom.

Preferably, wherein the olefins include 1-butene, 2-butene, isobutene or a mixture of two or more of these.

In FIG. 1 a schematic representation is given of a typical SA alkylation unit not according to the invention.

In FIG. 1, a hydrocarbon mixture, comprising olefin and isoparaffin is provided to reactor unit 100, e.g. a Stratco contactor, via conduit (e.g. a pipe) 105, through reactant inlet 107. Catalyst, SA or IL, is also provided to reactor unit 100 through conduit 110 and catalyst inlet 113. In reactor unit 100, the hydrocarbon mixture and catalyst are contacted under alkylation conditions. Through reactor effluent outlet 114, a reactor effluent comprising catalyst and hydrocarbons is withdrawn from reactor unit 100 and supplied via conduit 115 to settler unit 120 through reactor effluent inlet 122. In settler unit 120, an alkylate-comprising hydrocarbon phase and a catalyst phase separate under influence of gravity. The hydrocarbon phase is withdrawn from separator unit 120 via alkylate-comprising hydrocarbon phase outlet 123 and provided to fractionator unit 125 through conduit 130 and alkylate-comprising hydrocarbon phase inlet 133. From the bottom of fractionator unit 125, an alkylate-comprising product is retrieved through conduit 135. The alkylate product can for instance be used for fuel blending purposes. Additionally, an isoparaffin product is retrieved from fractionator unit 125, which is recycled via conduit 140 to become part of the hydrocarbon mixture in conduit 105. Other hydrocarbon-comprising streams (not shown) may also be retrieved from fractionator 125.

The catalyst phase is withdrawn from separator unit 120 through catalyst phase outlet 143 and can be recycled via catalyst phase recycle conduit 145 to reactor unit 100. A spent catalyst fraction may be withdrawn from the process via conduit 150. Additional fresh catalyst can be provided to reactor unit 100 via conduit 155

Figure 2:
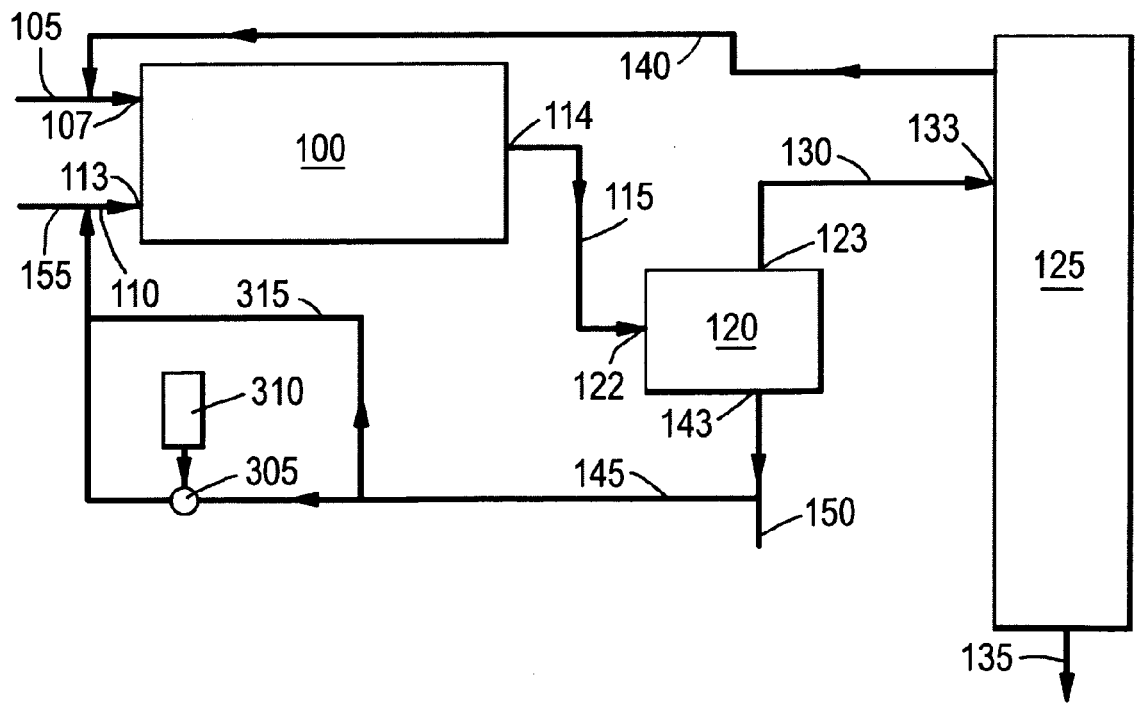

In FIG. 2, a schematic representation is given of a SA alkylation unit as described in FIG. 1, which was revamped using the method according to the invention, wherein a means for acid injection into the catalyst recycle means acid is provided. In FIG. 2, means 305 for injecting an acid, e.g. a gas injector, is provided in catalyst phase recycle conduit 145. Injector means 305 is fluidly connected to storage vessel 310, wherein an acid such as hydrogen chloride is stored. If required, a part of the recycled catalyst phase may bypass means 305 via bypass conduit 315. Bypass conduit 315 recombines with catalyst phase recycle conduit 145 downstream of acid injection means 305. In case a halohydrocarbon is injected instead of a acid, acid injection means 305 may be substituted by or complemented with a means for halohydrocarbon injection.

Where FIG. 1 or 2 refer to a SA alkylation unit, it will be appreciated that the same drawings could be used to represent an HF alkylation unit.

EXAMPLES

The invention is illustrated by the following non-limiting examples.

The acidic ionic liquids used in these examples were all synthesised by the China University of Petroleum Beijing according to the methods outlined in U.S. Pat. No. 7,285,698 and US 20040133056A1 and Chinese patent 02149296.4 or were commercial products purchased accordingly.

The composition of the alkylate in the implementations was established using gas chromatography, the catalytic activity being determined according to the butene transformation rate. The butene transformation rate (BTR) being defined as follows:

$$BTR = \frac{\text{(butene content at start} - \text{butene content upon completion} \times 100\%)}{\text{butene content at commencement}}$$

Example 1

An IL, based on $Et_3NHCl$ and $AlCl_3$ and $CuCl$, was used as the catalyst to catalyse the alkylation of isobutane. The catalyst inventory was 200 g. The alkylation reaction was performed at a reaction pressure of 0.5 MPa and a reaction temperature of 25° C. The feed to the alkylation reaction was a mixture of isobutane and 2-butene, whereby the isobutane to butene ratio was 20:1. Table 1 shows the obtained results for the alkylation reaction using the fresh catalyst.

As can be seen from table 1, when the quantity of feed processed per gram of ionic liquid reached 50 g, the activity of the catalyst exhibited a pronounced drop, once the quantity of raw material processed per gram of ionic liquid reached 60 g, the butene transformation approached 0, which indicates that the catalyst had totally lost its activity, at which stage 1120 g of alkylate had been obtained.

TABLE 1

| Feed processed g feed/g IL | BTR % | C8 selectivity Wt % | Ratio TMP/DMH |
|---|---|---|---|
| 10 | 100 | 85 | 22 |
| 20 | 100 | 86 | 14 |
| 30 | 100 | 86 | 14 |
| 40 | 100 | 86 | 14 |
| 50 | 76 | 80 | 13 |
| 60 | 0 | — | — |

Once it had been ascertained that the catalyst had completely lost activity, the supply of the alkylation raw materials was stopped. The ionic liquid was separated from the alkylation product, the inactive ionic liquid was returned to the reactor and mixed thoroughly with 15 g of 2-chloro-2-methyl-propane. After this had been completed, the alkylation raw materials were once again supplied to the reaction system under the above mentioned conditions and the alkylate product, i.e. the product produced with the regenerated catalyst, was collected and subjected to analysis, the results of which are shown in Table 2. It will be clear that the activity of the IL was restored and that the selectivity of the preferred product (C8 component) showed no pronounced change.

TABLE 2

| Feed processed g feed/g IL | BTR % | C8 selectivity Wt % | Ratio TMP/DMH |
|---|---|---|---|
| 10 | 100 | 87 | 14 |
| 20 | 100 | 87 | 14 |
| 30 | 100 | 87 | 15 |
| 40 | 100 | 87 | 15 |
| 50 | 100 | 87 | 15 |
| 60 | 54 | 77 | 13 |
| 70 | 0 | — | — |

The IL was subjected to the above procedure 10 times, under identical reaction conditions. The obtained results of the $10^{th}$ run are shown in Table 3.

The activity and C8 selectivity of the regenerated ionic liquid catalyst showed no pronounced changes and it may be assumed that it is possible to use this method to repeatedly treat and use ionic liquid catalysts.

TABLE 3

| Feed processed g feed/g IL | BTR % | C8 selectivity Wt % | Ratio TMP/DMH |
|---|---|---|---|
| 10 | 100 | 86 | 14 |
| 20 | 100 | 87 | 15 |
| 30 | 100 | 87 | 15 |
| 40 | 100 | 87 | 15 |
| 50 | 100 | 87 | 15 |
| 60 | 39 | 71 | 12 |
| 70 | 0 | — | — |

Example 2

An IL based on $Et_3NHCl$ and $AlBr_3$ was used as the catalyst in a continuous process to catalyse the alkylation of isobutane. The catalyst inventory was 30 kg. The alkylation reaction was performed at a reaction pressure of 0.5 MPa and a reaction temperature of 30° C., The feed to the alkylation reaction was a mixture of isobutane and 2-butene, isobutene and 1-butene, whereby the isobutane to butene ratio was 10:1. The feed charge rate was 12 kg/h, An alkylate yield rate of 2.4 kg/h was obtained.

3 kg/h of IL were intermittently separated off from the reaction system and placed in a mixer and thoroughly mixed with 2 g of hydrogen bromide and subsequently returned to the reaction system.

Table 4 shows the obtained results for the alkylation reaction using the intermittently rejuvenated catalyst. When the amount feed processed per gram of IL reached 1000 g, the catalyst had not lost activity and there was no change to the selectivity of the preferred product (C8 component).

TABLE 4

| Feed processed g feed/g IL | BTR % | C8 selectivity Wt % | Ratio TMP/DMH |
|---|---|---|---|
| 200 | 100 | 81 | 12 |
| 400 | 100 | 82 | 12 |
| 600 | 100 | 82 | 13 |
| 800 | 100 | 82 | 13 |
| 1000 | 100 | 82 | 13 |

Example 3

An IL based on $Et_3NHCl$ and $AlBr_3$ was used as the catalyst in a continuous process to catalyse the alkylation of isobutane. The catalyst inventory was 30 kg. The alkylation reaction was performed at a reaction pressure of 0.5 MPa and a reaction temperature of 30° C., The feed to the alkylation reaction was a mixture of isobutane and 2-butene, isobutene and 1-butene, whereby the isobutane to butene ratio was 10:1. The feed charge rate was 12 kg/h. An alkylate yield rate of 2.4 kg/h was obtained.

3 kg/h of IL were intermittently separated off from the reaction system and placed in a mixer and thoroughly mixed with 2 g of 6 g/h of 2-chloro-2-methyl-hexane and subsequently returned to the reaction system.

Table 5 shows the obtained results for the alkylation reaction using the intermittently rejuvenated catalyst. When the amount feed processed per gram of IL reached 1000 g, the catalyst had not lost activity and there was no change to the selectivity of the preferred product (C8 component).

TABLE 5

| Feed processed g feed/g IL | BTR % | C8 selectivity Wt % | Ratio TMP/DMH |
|---|---|---|---|
| 200 | 100 | 81 | 12 |
| 400 | 100 | 82 | 12 |
| 600 | 100 | 81 | 12 |
| 800 | 100 | 81 | 12 |
| 1000 | 100 | 81 | 12 |

Example 4

An IL based on $Et_3NHCl$ and $AlCl_3$ and CuCl was used as the catalyst in a continuous process to catalyse the alkylation of isobutane. The catalyst inventory was 200 g. The alkylation reaction was performed at a reaction pressure of 0.5 MPa and a reaction temperature of 25° C. The feed to the alkylation reaction was a mixture of isobutane and 2-butene, whereby the isobutane to butene ratio was 20:1. The feed charge rate was 500 g/h. An alkylate yield rate of 50 g/h was obtained 10 g/h of IL were intermittently separated off from the reaction system and placed in a mixer and thoroughly mixed with 0.03 g/h hydrogen chloride and subsequently returned to the reaction system.

Table 6 shows the obtained results for the alkylation reaction using the intermittently rejuvenated catalyst. When the amount feed processed per gram of IL reached 1000 g, the catalyst had not lost activity and there was no change to the selectivity of the preferred product (C8 component).

TABLE 6

| Feed processed g feed/g IL | BTR % | C8 selectivity Wt % | Ratio TMP/DMH |
|---|---|---|---|
| 200 | 100 | 85 | 14 |
| 400 | 100 | 86 | 14 |
| 600 | 100 | 86 | 15 |
| 800 | 100 | 86 | 15 |
| 1000 | 100 | 86 | 15 |

Example 5 (not According to the Invention)

An IL based on $Et_3NHCl$ and $AlCl_3$ and CuCl was used as the catalyst in a continuous process to catalyse the alkylation of isobutane. The catalyst inventory was 200 g. The alkylation reaction was performed at a reaction pressure of 0.5 MPa and a reaction temperature of 25° C. The feed to the alkylation reaction was a mixture of isobutane and 2-butene, whereby the isobutane to butene ratio was 20:1. The feed charge rate was 500 g/h. An alkylate yield rate of 50 g/h was obtained 10 g/h of IL were intermittently separated off from the reaction system and placed in a mixer and thoroughly mixed with 0.002 g/h hydrogen chloride and subsequently returned to the reaction system.

Table 7 shows the obtained results for the alkylation reaction using the intermittently rejuvenated catalyst. When the quantity of feed processed per g of IL reached 120 g, the catalyst had lost its activity. When compared to Example 4, it is clear that the usable life of the ionic liquid had not been extended.

TABLE 7

| Feed processed g feed/g IL | BTR % | C8 selectivity Wt % | Ratio TMP/DMH |
|---|---|---|---|
| 20 | 100 | 85 | 14 |
| 40 | 100 | 86 | 15 |
| 60 | 100 | 86 | 15 |
| 80 | 100 | 86 | 15 |
| 100 | 47 | 75 | 12 |
| 120 | 0 | — | — |

Example 6

An alkylation process was performed in three separate runs to mimic regular solids removal. In between each run the acidic ionic liquid catalyst was separated from the hydrocarbon phase and treated by removing solids and adding hydrogen chloride gas. The treated acidic ionic liquid catalyst was subsequently used in the following run.

The catalyst used was an ionic liquid catalyst comprising a coordinate anion derived from aluminium(III) chloride and copper(II) chloride) (ex China University of Petroleum Beijing)

At start-up, sufficient isobutane was provided to the test unit to allow for a molar ratio of isoparaffin to olefin in the reactor of above 95.

A hydrocarbon mixture of isobutane and butenes was provided together with the acidic ionic liquid catalyst to the alkylation reactor. The reactor had a volume of 0.4 liter.

The effluent of the alkylation reactor was separated in a settler and part of the hydrocarbon phase was sent to a fractionator, while the remainder of the hydrocarbon phase was recirculated to the reactor.

The alkylate was obtained from the bottom of the fractionator and tested to determine the motor RON and MON values.

An isobutane-comprising stream was recycled from the fractionator back to the hydrocarbon mixture.

The acidic ionic liquid catalyst phase obtained from the settler was recycled to the reactor. Periodically, i.e. between the runs, the acidic ionic liquid catalyst phase obtained from the settler was redirected to a disk centrifuge and centrifuged at 20000 rpm for 1 hour at a temperature of 50° C. The weight of solids produced was recorded. Following the solids removal, hydrogen chloride gas was added to the treated acidic ionic liquid catalyst at a pressure of approximately 5 bar at a temperature of 35° C., until no hydrogen chloride was consumed any more. The amount of hydrogen chloride consumed was recorded. The reaction condition and obtained results are listed in Table 8.

It will be clear that:

By providing means to recycle part of the hydrocarbon phase from the separator unit to the reaction recirculation a high isoparaffin to olefin molar ratio in the reactor is achieved. Recycling the isoparaffin from the fractionator alone cannot provide a high ratio of over 95.

By providing a second separator unit suitable for the removal of solids from the ionic liquid catalyst, approximately 1.5 kg of solids could be removed from the process. In case no solids removal would have taken place the 1.5 kg of solids would have accumulated in the reactor. By removing the solids, solids content is significantly reduced and the alkylate quality remains high.

By providing a means for acid injection into the catalyst recycle, the ionic liquid catalyst was intermittently rejuvenated, by reacting with hydrogen chloride. As a result catalyst activity and the alkylate quality remains high.

The observed differences in the obtained alkylate properties are caused by the differences in the alkylation temperature and isoparaffin to olefin ratio.

TABLE 8

| Run | | 1 | 2 | 3 |
|---|---|---|---|---|
| Reaction temperature, | ° C. | 35.7 | 41.0 | 35.9 |
| isobutane/butene ratio in feed | — | 5.3 | 11.3 | 11.6 |
| Ionic liquid/hydrocarbon ratio | — | 1.08 | 1.06 | 1.06 |
| Feed flow rate, | kg/h | 1.5 | 1.9 | 1.9 |
| Runtime, | h | 67 | 52 | 53 |
| C4 feed, | kg | 101.8 | 99.5 | 101.6 |
| Feed composition | mol % | | | |
| propane | | 0.1 | 0.1 | 0.1 |
| isobutane | | 56.7 | 50.6 | 52.1 |
| n-butane | | 8.7 | 10.9 | 9.0 |
| 1-butene | | 1.6 | 2.2 | 1.6 |
| 2-butene (trans) | | 20.8 | 22.0 | 23.4 |
| 2-butene (cis) | | 8.9 | 10.5 | 10.0 |
| i-butene | | 3.0 | 3.2 | 3.2 |
| Alkylate, | kg | 73.3 | 81.6 | 90.4 |
| Engine tested RON | — | 90.5 | 94.0 | 95.0 |
| Engine tested MON | — | 90.2 | 91.8 | 92.7 |
| Total solids* | g | 729.3 | 435 | 376 |
| Hydrogen chloride consumption | g | 143 | 95 | 104 |

*total weight of the solids slurry

Solids Analysis

The solids removed from the acidic ionic liquid catalyst phase were analysed. The size distribution was determined using a laser particle size analyser.

The results are shown in Table 9.

TABLE 9

| Run | | 1 | 2 | 3 |
|---|---|---|---|---|
| Percentage of particles having a diameter below 5μ | % | 99 | 99 | 99 |
| Percentage of particles having a diameter below 3μ | | 80 | 81 | 80 |

It should lastly be pointed out that the above implementations are purely for the sake of providing a description of the technical schemes to which this invention relates and as such are non-restrictive; any technician well acquainted with this field may make alterations or like-for-like exchanges of any aspect of the technical scheme of this invention, and as long as these do not exceed the scope of the technology revealed by this invention, they shall receive full protection according to scope of rights claimed by this invention.

What is claimed is:

1. A method for revamping an HF or sulphuric acid alkylation unit to an ionic liquid alkylation unit, wherein the HF or sulphuric acid alkylation unit comprises:
    a reactor for contacting catalyst and hydrocarbon reactants;
    a separator unit for separating a reactor effluent into a catalyst phase and an alkylate-comprising hydrocarbon phase;
    a fractionator unit for fractionating the alkylate-comprising hydrocarbon phase into at least one stream comprising alkylate; an
    a catalyst phase recycle conduit to recycle at least part of the catalyst phase from the separator unit to the reactor unit;
wherein the method for revamping comprises:
    replacing the HF or sulphuric acid catalyst in said HF or sulphuric acid alkylation unit with an ionic liquid catalyst;
    providing a means for injecting a hydrohalide and/or a halohydrocarbon into the catalyst phase recycle conduit; and
    providing a means for measuring pressure in the catalyst phase recycle conduit;
wherein the means for injecting is configured to add hydrohalide and/or halohydrocarbon to the catalyst phase in the catalyst phase recycle conduit in a plurality of injection steps, the means for measuring pressure is configured to measure pressure after each injection step, and the means for injecting is configured to add hydrohalide and/or halohydrocarbon to the catalyst phase in the catalyst phase recycle conduit until saturation and there is no decrease in measured pressure.

2. The method according to claim 1, wherein a bypass around the means for injecting a hydrohalide and/or the means for injecting a halohydrocarbon is provided to the catalyst phase recycle conduit to allow part of the catalyst phase to bypass the hydrohalide injection and/or halohydrocarbon injection.

3. The method according to claim 2, wherein the means for injecting a hydrohalide comprises a gas injector or a gas bubbler.

4. The method according to claim 1, wherein the hydrohalide is hydrogen chloride and any unreacted hydrogen chloride is purged from the ionic liquid alkylation unit with an inert gas.

5. A method for the production of alkylate comprising:
    a) alkylating a feed mixture comprising isobutane and an olefin in the presence of an ionic liquid catalyst under alkylation conditions to produce an effluent comprising a mixture of ionic liquid catalyst and a hydrocarbon phase comprising an alkylate;
    b) separating a catalyst phase comprising at least a portion of the ionic liquid catalyst from the effluent;
    c) injecting a hydrohalide or a halohydrocarbon containing 4 to 8 carbon atoms with the halogen being bound to a secondary carbon atom or tertiary carbon atom, into the catalyst in steps catalyst phase to rejuvenate the at least a portion of ionic liquid catalyst and measuring pressure of the catalyst phase after injecting the hydrohalide or the halohydrocarbon, wherein the hydrohalide or halohydrocarbon is injected into the catalyst phase in a plurality of injection steps, pressure is measured after each injection step, and the hydrohalide or halohydrocarbon is injected until the catalyst phase is saturated and there is no decrease in measured pressure; and
    d) recycling the rejuvenated ionic liquid catalyst into the alkylation step (a).

6. The method according to claim 5, wherein the catalyst phase and the hydrohalide or halohydrocarbon are mixed after each injection.

7. The method according to claim 5, wherein hydrohalide or halohydrocarbon is injected in an amount between 0.01-1 wt % of a total quantity of alkylate produced.

8. The method according to claim 7, wherein ionic liquid catalyst comprises cations derived from a hydrohalide amine containing alkyls, halogenated imidazole or halogenated pyridine, and anions selected from one or more metallic compounds.

9. The method according to claim 8, wherein the anions are selected from two or more metallic compounds, and wherein at least one of the two or more metallic compounds is selected from the group consisting of aluminum chloride and aluminum bromide, and at least one of the two or more metallic compounds is a halide, sulphate or nitrate of copper, iron, zinc, nickel, titanium or silver.

10. The method according to claim 9, wherein the hydrohalide is either hydrogen chloride or hydrogen bromide.

11. The method according to claim 9, wherein hydrohalide or halohydrocarbon is injected in an amount between 0.05-0.5 wt % of a total quantity of alkylate produced.

12. The method according to claim 5, wherein the halohydrocarbon is 2-bromobutane.

13. The method according to claim 5, wherein the halohydrocarbon is 2-chlorobutane.

14. The method according to claim 5, wherein the halohydrocarbon is 2-chloro-2-methylpropane.

15. The method according to claim 5, wherein the halohydrocarbon is 2-chloro-2-methylhexane.

16. The method according to claim 5, wherein the halohydrocarbon is 2-bromo-2-methylpropane.

17. The method according to claim 5, wherein the halohydrocarbon is 2-bromo-2-methylhexane.

* * * * *